(12) United States Patent
Popp et al.

(10) Patent No.: US 7,828,784 B2
(45) Date of Patent: Nov. 9, 2010

(54) ABSORBENT ARTICLES WITH REFASTENABLE SIDE SEAMS AND INTUITIVE DISPOSAL FEATURE

(75) Inventors: Robert L. Popp, Hortonville, WI (US); Mary P. Jordan, Neenah, WI (US); Christopher P. Olson, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 765 days.

(21) Appl. No.: 11/409,913

(22) Filed: Apr. 24, 2006

(65) Prior Publication Data
US 2007/0250029 A1    Oct. 25, 2007

(51) Int. Cl.
*A61F 13/15*    (2006.01)
(52) U.S. Cl. .................................. 604/387; 604/385.13
(58) Field of Classification Search ............ 604/385.01, 604/385.03, 385.13, 386–392
See application file for complete search history.

(56) References Cited

U.S. PATENT DOCUMENTS

| | | | |
|---|---|---|---|
| 4,581,772 A * | 4/1986 | Smith ............................. | 2/111 |
| 4,663,220 A | 5/1987 | Wisneski et al. | |
| 4,704,116 A | 11/1987 | Enloe | |
| 4,720,415 A | 1/1988 | Vander Wielen et al. | |
| 4,834,742 A | 5/1989 | Wilson et al. | |
| 4,940,464 A | 7/1990 | Van Gompel et al. | |
| 5,046,272 A | 9/1991 | Vogt et al. | |
| 5,087,253 A * | 2/1992 | Cooper .................. | 604/385.15 |
| 5,104,116 A | 4/1992 | Pohjola | |
| 5,176,671 A | 1/1993 | Roessler et al. | |
| 5,224,405 A | 7/1993 | Pohjola | |
| 5,226,992 A | 7/1993 | Morman | |
| 5,401,275 A * | 3/1995 | Flug et al. .................... | 604/391 |
| 5,766,389 A | 6/1998 | Brandon et al. | |
| 6,287,287 B1 | 9/2001 | Elsberg | |
| 6,447,497 B1 * | 9/2002 | Olson ......................... | 604/389 |
| 6,454,751 B1 | 9/2002 | Olson | |
| 2002/0095131 A1 | 7/2002 | Olson | |
| 2003/0060794 A1 | 3/2003 | Olson | |
| 2004/0022993 A1 | 2/2004 | Wildeman | |
| 2006/0069379 A1 | 3/2006 | Van Gompel et al. | |

FOREIGN PATENT DOCUMENTS

GB        2 303 045 A        2/1997

* cited by examiner

*Primary Examiner*—Michele Kidwell
(74) *Attorney, Agent, or Firm*—H. Michael Kubicki

(57) ABSTRACT

A disposable absorbent article including a pair of first fasteners, at least a portion of each first fastener being situated inboard from each longitudinal side edge in the first waist region, each first fastener being adapted to engage at least a portion of the inner surface of the second waist region, each first fastener comprising a resilient material. The disposable absorbent article also includes a disposal fastener, at least a portion of the disposal fastener being situated inboard from the longitudinal side edge in the second waist region, the disposal fastener adapted to engage at least a portion of the outer surface, the disposal fastener comprising a resilient material.

23 Claims, 10 Drawing Sheets

ABSORBENT ARTICLES WITH REFASTENABLE SIDE SEAMS AND INTUITIVE DISPOSAL FEATURE

BACKGROUND OF THE INVENTION

Pant-like disposable garments, such as adult incontinence wear, infant and children's diapers, swim wear and training pants, typically have adhesive or mechanical fasteners on the sides for donning and removal, or else rely on a stretchable waist opening and leg openings to slide on and off the wearer.

Refastenable seams, including, for example, mechanical fasteners such as hook and loop fasteners, have been found to be particularly beneficial when used in conjunction with pant-like disposable garments. Refastenable seams allow for the garment to be easily applied and removed, as well as periodically opened to check for exudates and closed if no exudates are found. For example, pant-like, "pull-on" style disposable garments can have one or more prefastened, refastenable side seams. Such prefastened, refastenable side seams perform at least two useful functions. First, they maintain the garment in a pant-like configuration during donning and removal. Second, they allow for easy inspection of the internal condition of the garment while on the wearer, and allow for refastening if it is not yet necessary to remove the garment. One means of providing a prefastened, refastenable side seam in a pant-like disposable garment is through the use of a mechanical fastener, such as a hook material. In traditional pant-like disposable garments consideration has generally not been given to disposal of the soiled garment, and more particularly, how exudates may be contained within the garment after it has been removed.

Thus, it would be desirable to have a disposable absorbent article that provides the garment-like look of a traditional training pant, includes fastening components to allow application like either a diaper or a pant, minimizes the likelihood of the fastening components coming into contact with the skin of the wearer and provides an easy to use, intuitive diaper-like disposal feature.

SUMMARY OF THE INVENTION

In response to the foregoing need, the present inventor undertook intensive research and development efforts that resulted in the discovery of an absorbent article. One version of the present invention includes a prefastened disposable absorbent article having opposed longitudinal side edges, opposed lateral end edges, a first waist region, a second waist region and a crotch region which extends between and connects the first waist region and the second waist region. The disposable absorbent article has an inner surface, an outer facing surface, an absorbent assembly, and a pair of first fasteners. At least a portion of each first fastener is situated inboard from each longitudinal side edge in the first waist region. Each first fastener is adapted to engage at least a portion of the inner surface of the second waist region. Each first fastener comprises a resilient material. The disposable absorbent article also has a disposal fastener. At least a portion of the disposal fastener is situated inboard from the longitudinal side edge in the second waist region. The disposal fastener is adapted to engage at least a portion of the outer surface. The disposal fastener comprises a resilient material. Further, the disposal fastener contacts at least a portion of one of the first fasteners when the absorbent article is prefastened.

Another version of the present invention provides a prefastened disposable absorbent article having opposed longitudinal side edges, opposed lateral end edges, a first waist region, a second waist region and a crotch region which extends between and connects the first waist region and the second waist region. The disposable absorbent article includes an inner surface, an outer surface, an absorbent assembly and a pair of first fasteners. At least a portion of each first fastener is situated inboard from each longitudinal side edge in the first waist region. Each first fastener is adapted to engage at least a portion of the inner surface of the second waist region. Each first fastener comprises a resilient material. The disposable absorbent article also includes a disposal fastener. At least a portion of the disposal fastener is situated inboard from the longitudinal side edge in the second waist region. The disposal fastener is to engage at least a portion of the outer surface. The disposal fastener comprises a resilient material. Further, with the lateral end edge in the first waist region and the lateral end edge in the second waist region aligned, the pair of first fasteners and the disposal fastener do not longitudinally overlap another.

Still another version of the present invention includes an absorbent article, comprising an absorbent chassis defining a longitudinal axis, a transverse axis, front and back waist edges parallel to the transverse axis, opposite side edges extending between the front and back waist edges, a front waist region contiguous with the front waist edge, a back waist region contiguous with the back waist edge, a crotch region which extends between and interconnects the front and back waist regions, an inner surface and an outer surface. The absorbent chassis also comprises a rectangular composite structure having opposite linear side edges parallel to the longitudinal axis and opposite linear end edges parallel to the transverse axis. The composite structure comprises a bodyside liner, an outer cover bonded to the bodyside liner, and an absorbent assembly disposed between the bodyside liner and the outer cover. The absorbent chassis also comprises first and second front side panels bonded to the composite structure in the front waist region, each front side panel having a distal edge, an interior portion between the distal edge and the composite structure, a waist end edge parallel to the transverse axis and forming part of the front waist edge, and a leg end edge forming part of the side edge. The front side panels have an average length dimension that is about 20 percent or greater of the overall length dimension of the absorbent article. The absorbent chassis also comprises first and second back side panels bonded to the composite structure in the back waist region and longitudinally spaced from the first and second front side panels, each back side panel having a distal edge, an interior portion between the distal edge and the composite structure, a waist end edge parallel to the transverse axis and forming part of the back waist edge, and a leg end edge forming part of the side edge. The back side panels have an average length dimension that is about 20 percent or greater of the overall length dimension of the absorbent article. The absorbent chassis also comprises a pair of first fasteners disposed on the first and second front side panels, each first fastener being adapted to engage at least a portion of the inner surface of the back waist region, each first fastener comprising a resilient material. The first fasteners have a length in the longitudinal direction that is greater than about 50% of the length dimension of the distal edge of the front side panels. The absorbent chassis also comprises a pair of disposal fasteners disposed on the first and second front side panels, each disposal fastener adapted to engage at least a portion of the outer surface, each disposal fastener comprising a resilient material. The disposal fasteners have a length in the longitudinal direction that is less than about 25% of the length dimension of the distal edge of the back side panels.

Further the transverse distance between the pair of first fasteners is substantially equal to the transverse distance between the pair of disposal fasteners.

DEFINITIONS

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Graphic" refers to any design, pattern, or the like that is visible on an absorbent article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Integral" is used to refer to various portions of a single unitary element rather than separate structures bonded to or placed with or placed near one another.

"Inward" and "outward" refer to positions relative to the center of an absorbent article, and particularly transversely and/or longitudinally closer to or away from the longitudinal and transverse center of the absorbent article.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use.

"Permanently bonded" refers to the joining, adhering, connecting, attaching, or the like, of two elements of an absorbent garment such that the elements tend to be and remain bonded during normal use conditions of the absorbent garment.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a nonsoftened condition when cooled to room temperature.

These terms may be defined with additional language in the remaining portions of the specification.

BRIEF DESCRIPTION OF THE DRAWINGS

The above-mentioned and other features of the present invention and the manner of attaining them will become more apparent, and the invention itself will be better understood by reference to the following description and the accompanying drawings, wherein similar features in different figures have been given the same reference numeral.

DETAILED DESCRIPTION OF THE DRAWINGS

Figure 1A:
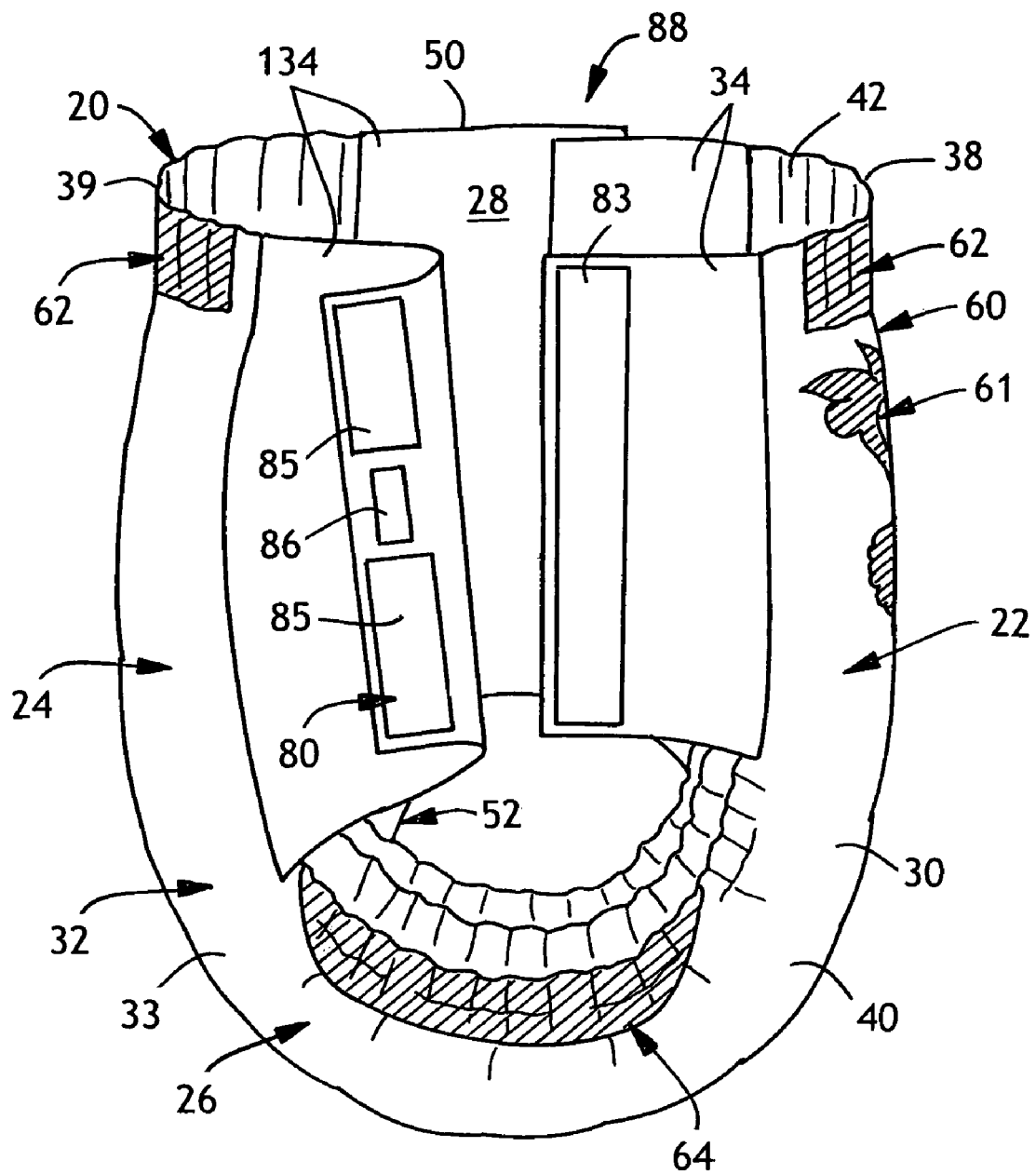
FIG. 1A illustrates a side view of one type of disposable absorbent article incorporating the principles of the present invention, where the fastening system is shown engaged on one side of the absorbent article and disengaged on the other side of the absorbent article.

The principles of the present invention can be incorporated into any suitable disposable absorbent article. Examples of such suitable articles include diapers, training pants, feminine hygiene products, incontinence products, other personal care or health care garments, or the like. For ease of explanation, the description hereafter will be in terms of a child's training pant.

With reference to FIG. 1, a disposable absorbent article, such as a training pant 20, is illustrated in a partially fastened condition. The training pant 20 comprises an absorbent chassis 32 and a fastening system 80. The absorbent chassis 32 defines a first waist region and a second waist region. More specifically, the absorbent chassis 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIGS. 2 and 3, the absorbent chassis 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39.

The illustrated absorbent chassis 32 comprises a rectangular composite structure 33, a pair of transversely opposed front side panels 34, and a pair of transversely opposed back side panels 134. The composite structure 33 and side panels 34 and 134 may be integrally formed or comprise two or more separate elements, as shown in FIGS. 1A-1E. The illustrated composite structure 33 comprises an outer cover 40, a bodyside liner 42 (FIGS. 1A-1E and 3) which is connected to the outer cover in a superposed relation, an absorbent assembly 44 (FIG. 3) which is located between the outer cover and the bodyside liner, and a pair of containment flaps 46 (FIG. 3). The rectangular composite structure 33 has opposite linear end edges 45 that form portions of the front and back waist edges 38 and 39, and opposite linear side edges 47 that form portions of the side edges 36 of the absorbent chassis 32 (FIGS. 2 and 3). For reference, arrows 48 and 49 depicting the orientation of the longitudinal axis and the transverse axis, respectively, of the training pant 20 are illustrated in FIGS. 2 and 3.

With the training pant 20 in the fastened position as partially illustrated in FIGS. 1A-1E, the front and back waist regions 22 and 24 are joined together to define a three-dimensional pant configuration having a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The front and back side panels 34 and 134 comprise the portions of the training pant 20 which, when worn, are positioned on the hips of the wearer.

The front waist region 22 of the absorbent chassis 32 includes the transversely opposed front side panels 34 and a front center panel 35 (FIGS. 2 and 3) positioned between and interconnecting the side panels. The back waist region 24 of the absorbent chassis 32 includes the transversely opposed back side panels 134 and a back center panel 135 (FIGS. 2 and 3) positioned between and interconnecting the side panels. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52.

The absorbent chassis 32 is configured to contain and/or absorb any body exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably includes a front waist elastic member 54, a rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38 and 39, and can extend over part or all of the waist edges. The leg elastic members 58 are desirably operatively joined to the outer cover 40 and/or bodyside liner 42 along the opposite side edges 36 and positioned in the crotch region 26 of the training pant 20. The leg elastic members 58 are desirably longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 are desirably located adjacent the longitudinally innermost parts of the front side panels 34, and the back terminal points 65 are desirably located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from LYCRA from INVISTA of Wichita, Kans.

The outer cover 40 desirably comprises a material that is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as a liquid impermeable inner layer, or a single layer liquid impermeable outer cover 40, is a 1.0 mil polyethylene film commercially available from Pliant Corporation of South Plainfield, N.J., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn., U.S.A.

As shown in FIGS. 1A-1E and 2, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young girls, includes a registered outer cover graphic 60. In this design, the registered graphic 60 includes simulated a primary pictorial image 61, simulated waist ruffles 62, and simulated leg ruffles 64. The primary pictorial image 61 includes a rainbow, sun, clouds, animal characters, wagon and balloons. Any suitable design can be utilized for a training pant intended for use by young girls, so as to be aesthetically and/or functionally pleasing to them and the caregiver. The appearance-related components are desirably positioned on the training pant 20 at selected locations, which can be carried out using the methods disclosed in U.S. Pat. No. 5,766,389 issued Jun. 16, 1998 to Brandon et al., which is incorporated herein by reference. The primary pictorial image 61 is desirably positioned in the front waist region 22 along the longitudinal centerline of the training pant 20.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can comprise elastomeric materials, it can be desirable in some embodiments for the composite structure to be generally inelastic, where the outer cover, the bodyside liner and the absorbent assembly comprise materials that are generally not elastomeric.

The absorbent assembly 44 (FIG. 3) is positioned between the outer cover 40 and the bodyside liner 42, which components can be joined together by any suitable means such as adhesives as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and comprises a blend of wood pulp fluff and superabsorbent material. One preferred type of fluff is identified with the trade designation CR1654, available from Bowater of Greenville, S.C., USA, and is a bleached, highly absorbent sulfate wood pulp containing primarily soft wood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that maintains the integrity and/or shape of absorbent assembly.

The absorbent chassis 32 can also incorporate other materials that are designed primarily to receive, temporarily store, and/or transport liquid along the mutually facing surface with absorbent assembly 44, thereby maximizing the absorbent capacity of absorbent assembly. One suitable material is referred to as a surge layer (not shown) and comprises a material having a basis weight of about 50 grams per square meter, and comprising a through-air-bonded-carded web of a homogenous blend of 60 percent 3 denier bicomponent fiber comprising a polyester core/polyethylene sheath, commercially available from BASF Corporation, and 40 percent 6 denier polyester fiber, commercially available from Hoechst Celanese Corporation, in Portsmouth, Va., U.S.A.

As noted previously, the illustrated training pant 20 has front and back side panels 34 and 134 disposed on each side of the absorbent chassis 32. These transversely opposed front side panels 34 and transversely opposed back side panels 134 can be permanently bonded to the composite structure 33 of the absorbent chassis 32 in the respective front and back waist regions 22 and 24, and are releasably attached to one another by the fastening system 80. More particularly, as shown best in FIGS. 2 and 3, the front side panels 34 can be permanently bonded to and extend transversely beyond the linear side edges 47 of the composite structure 33 in the front waist region 22 along attachment lines 66, and the back side panels 134 can be permanently bonded to and extend transversely beyond the linear side edges of the composite structure in the back waist region 24 along attachment lines 66. The side panels 34 and 134 may be attached using attachment means known to those skilled in the art such as adhesive, thermal or ultrasonic bonding. The side panels 34 and 134 can also be formed as a portion of a component of the composite structure 33, such as the outer cover or the bodyside liner.

The illustrated side panels 34 and 134 each define a distal edge 68 that is spaced from the attachment line 66, a leg end edge 70 disposed toward the longitudinal center of the training pant 20, and a waist end edge 72 disposed toward a longitudinal end of the training pant. The leg end edge 70 and waist end edge 72 extend from the side edges 47 of the composite structure 33 to the distal edges 68. The leg end edges 70 of the side panels 34 and 134 form part of the side edges 36 of the absorbent chassis 32. In the back waist region 24, the leg end edges 70 are desirably although not necessarily angled relative to the transverse axis 49 to provide greater coverage toward the back of the pant as compared to the front of the pant. The waist end edges 72 are desirably parallel to the transverse axis 49. The waist end edges 72 of the front side panels 34 form part of the front waist edge 38 of the absorbent chassis 32, and the waist end edges 72 of the back side panels 134 form part of the back waist edge 39 of the absorbent chassis.

In particular embodiments for improved fit and appearance, the side panels 34 and 134 desirably have an average length dimension measured parallel to the longitudinal axis 48 that is about 15 percent or greater, and particularly about 20 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 have a continually decreasing length dimension moving from the attachment line 66 to the distal edge 68, as is best shown in FIGS. 2 and 3.

Each of the side panels 34 and 134 can include one or more individual, distinct pieces of material. In particular embodiments, for example, each side panel 34 and 134 can include first and second side panel portions that are joined at a seam, with at least one of the portions comprising an elastomeric material (see FIG. 7). Still alternatively, each individual side panel 34 and 134 can include a single piece of material which is folded over upon itself along an intermediate fold line (not shown).

The side panels 34 and 134 desirably comprise an elastic material capable of stretching in a direction generally parallel to the transverse axis 49 of the training pant 20. In particular embodiments, the front and back side panels 34 and 134 may each comprise an interior portion 78 disposed between the distal edge 68 and the respective front or back center panel 35 or 135. In the illustrated embodiment, the interior portions 78 are disposed between the distal edges 68 and the side edges 47 of the rectangular composite structure 33. The elastic material of the side panels 34 can be disposed in the interior portions 78 to render the side panels elastomeric in a direction generally parallel to the transverse axis 49. Most desirably, each side panel 34 is elastomeric from the waist end edge 72 to the leg end edge 70. More specifically, individual samples of side panel material, taken between the waist end edge 72 and the leg end edge 70 parallel to the transverse axis 49 and having a length from the attachment line 66 to the distal edge 68 and a width of 2 centimeters, are all elastomeric.

Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Mormon; and U.S. Pat. No. 4,720,415 issued Jan. 19, 1988 to Taylor et al.; all of which are incorporated herein by reference. Alternatively, the side panel material may comprise other woven or nonwoven materials, such as those described above as being suitable for the outer cover 40 or bodyside liner 42, or stretchable but inelastic materials.

The training pant 20 according to the present invention also includes a fastening system 80 for securing the training pant about the waist of the wearer (FIGS. 1A-1E, 2 and 3). The illustrated fastening system 80 includes first and second fastening components 82 and 83 that are adapted to refastenably connect to first and second mating fastening components 84 and 85. In one embodiment, one surface of each of the first and second fastening components 82 and 83 comprises a plurality of engaging elements that project from that surface. The engaging elements of these fastening components 82 and 83 are adapted to repeatedly engage and disengage the engaging elements of the mating fastening components 84 and 85.

The training pant 20 according to the present invention also includes a disposal fastener 86 for securing the training pant in a closed configuration after the training pant has been removed from the child (FIGS. 1A-1E, 2, 3 and 4). This may be advantageous for containing the contents of a soiled training pant 20 prior to depositing in the garbage or other an appropriate receptacle. The training pant 20 may contain a single disposal fastener 86, or alternatively a pair of disposal fasteners 86 as illustrated in FIGS. 2, 3, 4 and 8. The illustrated disposal fastener 86 is adapted to engage at least a portion of the outer surface 30 such as the outer layer of the outer cover 40. The disposal fastener 86 may be adapted to engage a portion of the outer surface 30 in the front waist region 22, back waist region 24 or the crotch region 26. The disposal fastener 86 may be adapted such that it is does not functionally engage with a portion of he outer surface 30 when the garment is prefastened. Alternatively, the disposal fastener 86 may be adapted to refastenably connect to a mating disposal fastener 87 (FIG. 1B) when the garment is prefastened.

In one particular embodiment, the first and second fastening components 82 and 83 and the disposal fastener 86 each comprise hook type fasteners and the first and second mating fastening components 84 and 85 and the mating disposal fastener 87 each comprise complementary loop type fasteners. The first and second fastening components 82, 83 and the disposal fastener 86 may comprise the same material, such as an identical hook. Alternatively, the first and second fastening components 82, 83 and the disposal fastener 86 may comprise a similar material, such as a small hook, and a large hook, or a stiff hook and a less stiff hook. Although the illustrated embodiments show the back waist region 24 overlapping the front waist region 22, which is convenient, the training pant 20 can also be configured so that the front waist region overlaps the back waist region.

Loop type fasteners typically comprise a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549. The loop material can be an integral portion of the outer surface or inner surface of the side panel rather than a separated material or structure.

Hook type fasteners typically comprise a fabric or material having a base or backing structure and a plurality of hook members extending upwardly from at least one surface of the backing structure. In contrast to the loop type fasteners which desirably comprise a flexible fabric, the hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82 and 83 or the mating fastening components 84 and 85 are available from Velcro Industries B.V., Amsterdam, Netherlands or affiliates thereof, and are identified as Velcro HTH-829 with a uni-directional hook pattern and having a thickness of about 0.089 millimeters (3.5 mils) and HTH-851 with a uni-directional hook pattern and having a thickness of about 0.051 millimeters (2 mils).

With particular reference to FIG. 2, the first and second fastening components 82 and 83 are desirably disposed on the outer surface 30 of the training pant 20 in the front waist region 22. The first and second fastening components 82 and 83 are desirably positioned along the distal edges 68 of the front side panels 34, and abutting or adjacent to the waist end edge 72. In certain embodiments, for example, the first and second fastening components 82 and 83 are located within about 2 centimeters, and more particularly within about 1 centimeter, of the distal edges 68, the waist end edges 72, and the leg end edges 70.

With particular reference to FIG. 2, the first and second mating fastening components 84 and 85 are disposed on the inner surface 28 of the training pant 20 in the back waist region 24. The first and second mating fastening components 84 and 85 are sized to receive the first and second fastening components 82 and 83 and are desirably positioned along the distal edges 68 of the back side panels 134, and abutting or adjacent to the waist end edge 72. In certain embodiments, for example, the first and second mating fastening components 84 and 85 are located within about 2 centimeters, and more particularly within about 1 centimeter, of the distal edges 68, the waist end edges 72, and the leg end edges 70. Where the fastening components 82, 83 comprise hook type fasteners disposed on the outer surface 30 and the mating fastening components 84 and 85 comprise loop type fasteners disposed on the inner surface 28, the mating fastening components can be sized larger than the fastening components to ensure coverage of the rigid, outwardly-directed hooks.

The use of outwardly-directed hooks for the fastening components 82, 83 may provide an advantage in that if the front side panel 34 and the back side panel 134 are misaligned the skin of the wearer is more likely to be expose to the inwardly-directly, relatively flexible loop and less likely to be exposed to the outwardly-directed relatively more rigid hook. This orientation is less likely to cause skin irritations than if the components 82, 83 and 84, 85 were reversed. Further, the orientation shown in FIG. 2 results in a training pant 20 that is fastened with the back waist region 24 overlapping the front waist region 22.

This orientation does present an opportunity. Specifically, caregivers who are accustomed to using conventional diapers, upon removing a soiled diaper, may roll the front of the diaper toward the back of the diaper, isolating the exudates within the diaper. With a conventional diaper, the caregiver may then utilize the diaper's inwardly facing, resilient fasteners to maintain the diaper in a wrapped configuration by fastening them into the outer surface. When the caregiver utilizes the similar disposal techniques on the training pant 20, the fastening components 82, 83 may be located within the rolled article, and may not be accessible to maintain the training pant 20 in a wrapped configuration. The disposal fastener 86 of the present invention provides a solution to this opportunity, by providing a disposal fastener 86 that is adapted to engage at least a portion of the outer surface 30, providing the care giver with an intuitive, diaper-like disposal method.

Because the disposal fastener 86 is not primarily designed to secure the training pant 20 about the waist of the wearer, the size, shape, configuration and material design may be tailored for this specific use. The disposal fastener 86 may be designed to minimize potential irritation from skin contact without having to balance the need for the level of fastening security required by the fastening system 80.

For the refastenable seams 88 to be located at the sides of the wearer, it is particularly desirable for the transverse distance between the first and second fastening components 82 and 83 to be substantially equal to the transverse distance between the first and second mating fastening components 84 and 85. The transverse distance between a set of fasteners is the distance measured parallel to the transverse axis 49 between the longitudinal centerlines of the fasteners, measured with the side panels 34 and 134 in an unstretched condition. Further, it may be desirable for the transverse distance between the first and second fastening components 82 and 83 to be substantially equal to the transverse distance between the pair of disposal fasteners 86.

The fastening components, mating fastening components, disposal fasteners and mating disposal fasteners 82-87 can be adhered to the side panels 34 and 134 by any means known to those skilled in the art such as adhesive bonds, sonic bonds or thermal bonds. In an alternative embodiment, the training pant 20 includes only a single mating fastening component disposed in the front waist region 22 for refastenably connecting the fastening components 82 and 83 (not shown). The fastening components, mating fastening components, disposal fasteners and mating disposal fasteners 82-87 may be provided by a single piece of material, for example the fastening component 83 in FIG. 1D. Alternatively, the fastening components, mating fastening components, disposal fasteners and mating disposal fasteners 82-87 may be provided by a plurality of pieces of material, for example the fastening component 83 in FIG. 1B depending on the specific design of the absorbent article.

In a further alternative embodiment, the fastening components, disposal fasteners, mating disposal fasteners and mating fastening components can comprise integral portions of the side panels. For instance, the elastomeric back side panels 134 can function as a mating fastening component in that they can comprise a material that is releasably engageable with the mating fastening components 84 and 85 (FIG. 1E). The first and second mating fastening components 84 and 85 and disposal fasteners 86 are desirably rectangular, although they may alternatively be square, round, oval, curved or otherwise nonrectangularly shaped.

When the fastening components and the mating fastening components 82-85 are releasably engaged, the side edges 36 of the absorbent chassis 32 in the crotch region 26 define the leg openings 52, and the waist edges 38 and 39 of the absorbent chassis, including the waist end edges 72 of the side panels, define the waist opening 50. For improved formation of the leg openings 52, it is desirable in some embodiments for the front side panels 34 to be longitudinally spaced from the back side panels 134 (see FIGS. 2 and 3). For example, the front side panels 34 can be longitudinally spaced from the back side panels 134 by a distance equal to about 20 percent or greater, particularly from about 20 to about 70 percent, and more particularly from about 35 to about 50 percent, of the overall length dimension of the absorbent article.

When connected, the fastening components and the mating fastening components 82-85 form a refastenable seam 88 (FIG. 1A-1E). In particular embodiments, each of the fastening components and the mating fastening components 82-85 defines a length dimension aligned generally parallel with the longitudinal axis 48 of the training pant 20 and a width dimension aligned generally parallel with the transverse axis 49 of the training pant. For a child of about 9 to about 15 kilograms (20-30 pounds), for example, the length dimension of the fastening components and mating fastening components is desirably from about 5 to about 13 centimeters, such as about 10 centimeters, and the width dimension is desirably from about 0.5 to about 3 centimeters, such as about 1 centimeter. The fastening components and the mating fastening components desirably have a length-to-width ratio of about 2 or greater, such as about 2 to about 25, and particularly about 5 or greater, such as about 5 to about 8.

In particular embodiments, each of the disposal fasteners 86 and the mating disposal fasteners 87 defines a length dimension aligned generally parallel with the longitudinal axis 48 of the training pant 20 and a width dimension aligned generally parallel with the transverse axis 49 of the training pant. For example, the length dimension of the disposal fasteners 86 and mating disposal fasteners 87 is desirably from about 0.25 to about 4 centimeters, such as about 2 centimeters, and the width dimension is desirably from about 0.5 to about 3 centimeters, such as about 1 centimeter. The disposal fastenings and the mating disposal fastenings desirably have a length-to-width ratio of about 2 or less, such as about 0.25 to about 1.9, and particularly about 1.5 or less, such as about 0.5 to about 1.

The fastening components 82, 83 may have a length dimension greater than about 50% of length dimension of the distal edge 68 of the side panel 34, 134, specifically greater than about 65%, or greater than about 80% of the length dimension of the distal edge 68 of the side panel 34, 134. The disposal fastener 86 may have a length dimension less than about 25% of length dimension of the distal edge 68 of the side panel 34, 134, specifically less than about 20%, or less than about 15% of the length dimension of the distal edge 68 of the side panel 34, 134.

The disposal fastener 86 may be located anywhere along the length of the distal edge 68 of the side panel 34, 134. For instance, as illustrated in FIGS. 1A, 1B, 1E 2, 3, 4, 7 and 8, the disposal fastener 86 may be centrally located along the distal edge 68 of the side panel 34, 134. As illustrated in FIG. 1C, the disposal fastener 86 may be located relatively close to the waist opening 50 along the distal edge 68 of the side panel 34, 134. Further, as illustrated in FIG. 1D, the disposal fastener 86 may be located relatively close to the leg opening 52 along the distal edge 68 of the side panel 34, 134.

In particular embodiments, each of the fastening components and the mating fastening components 82-85 defines an area, and each of the disposal fasteners and mating disposal fasteners 86, 87 defines an area. Further the ratio of the area of the first fastening component 82, 83 to the area of the disposal fastener 86 may be greater than about 3:1, alternatively greater than about 5:1, or alternatively greater than about 6:1. This ratio is a result of the desire to have a secure fastener, which may require a large area along with the desire to have a relatively discrete disposal fastener which is less likely to contact and irritate the skin.

Figure 1B:
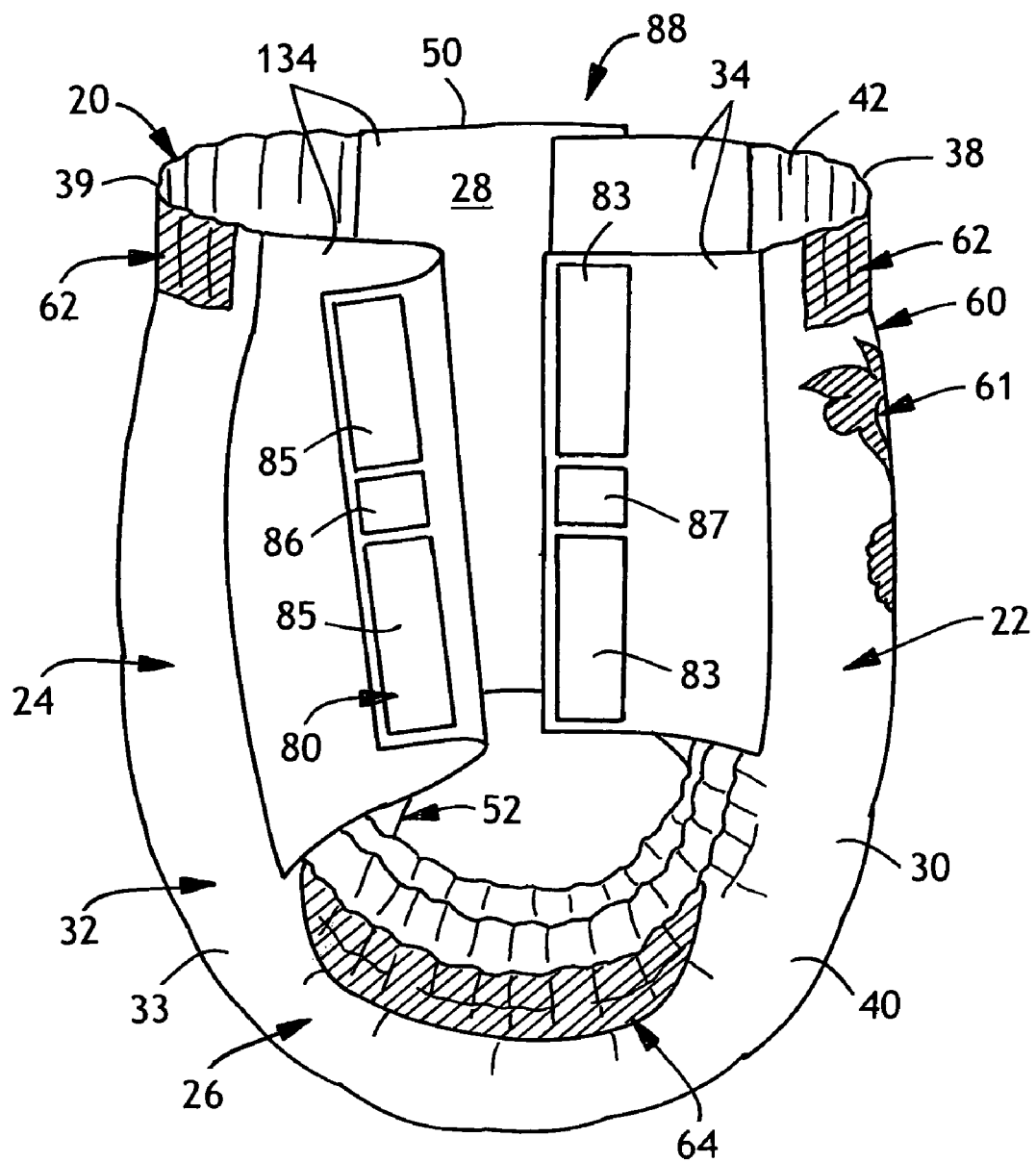
FIG. 1B illustrates a side view of an alternative disposable absorbent article incorporating the principles of the present invention, where the fastening system is shown engaged on one side of the absorbent article and disengaged on the other side of the absorbent article.
Figure 1C:
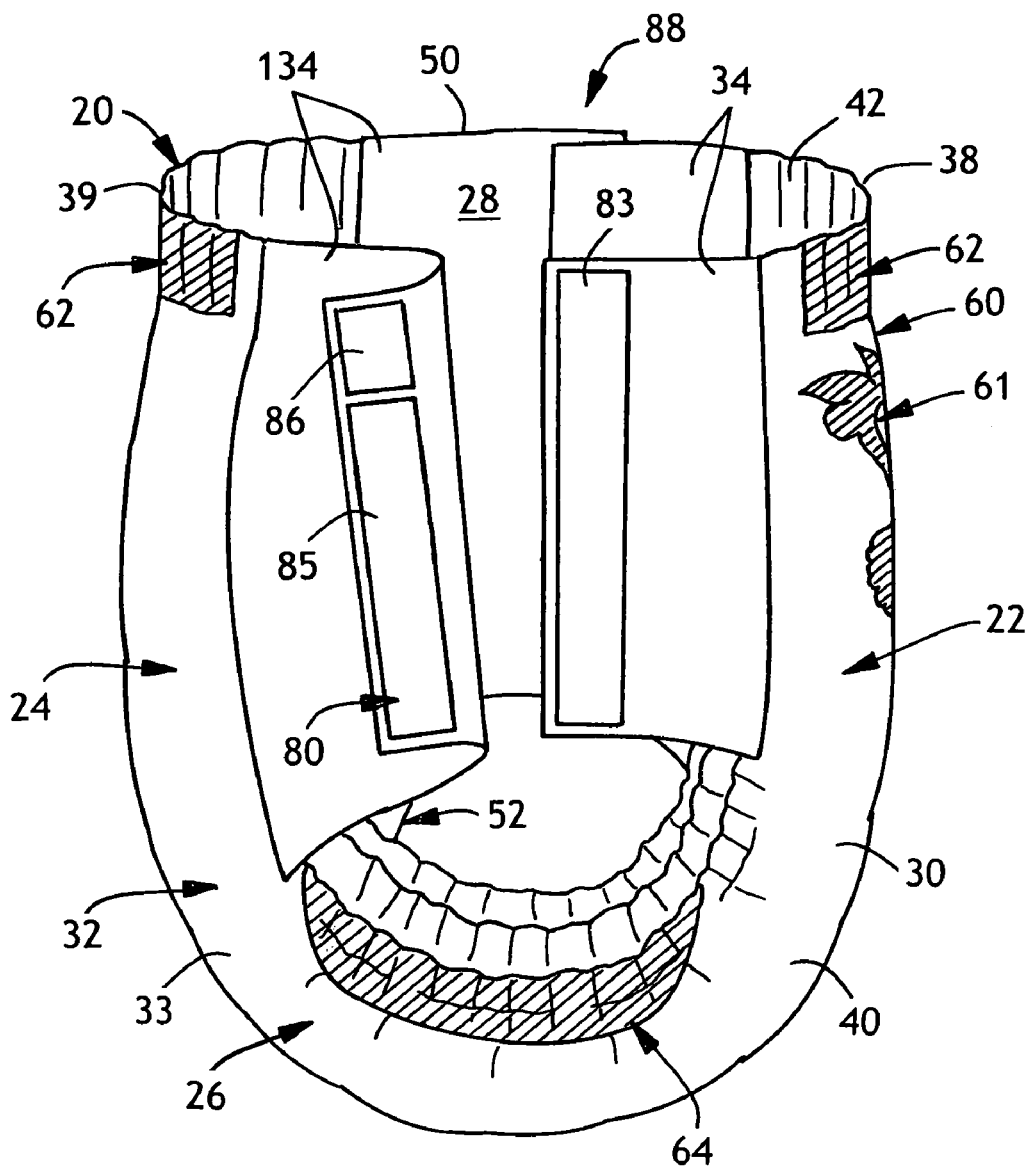
FIG. 1C illustrates a side view of an alternative disposable absorbent article incorporating the principles of the present invention, where the fastening system is shown engaged on one side of the absorbent article and disengaged on the other side of the absorbent article.
Figure 1D:
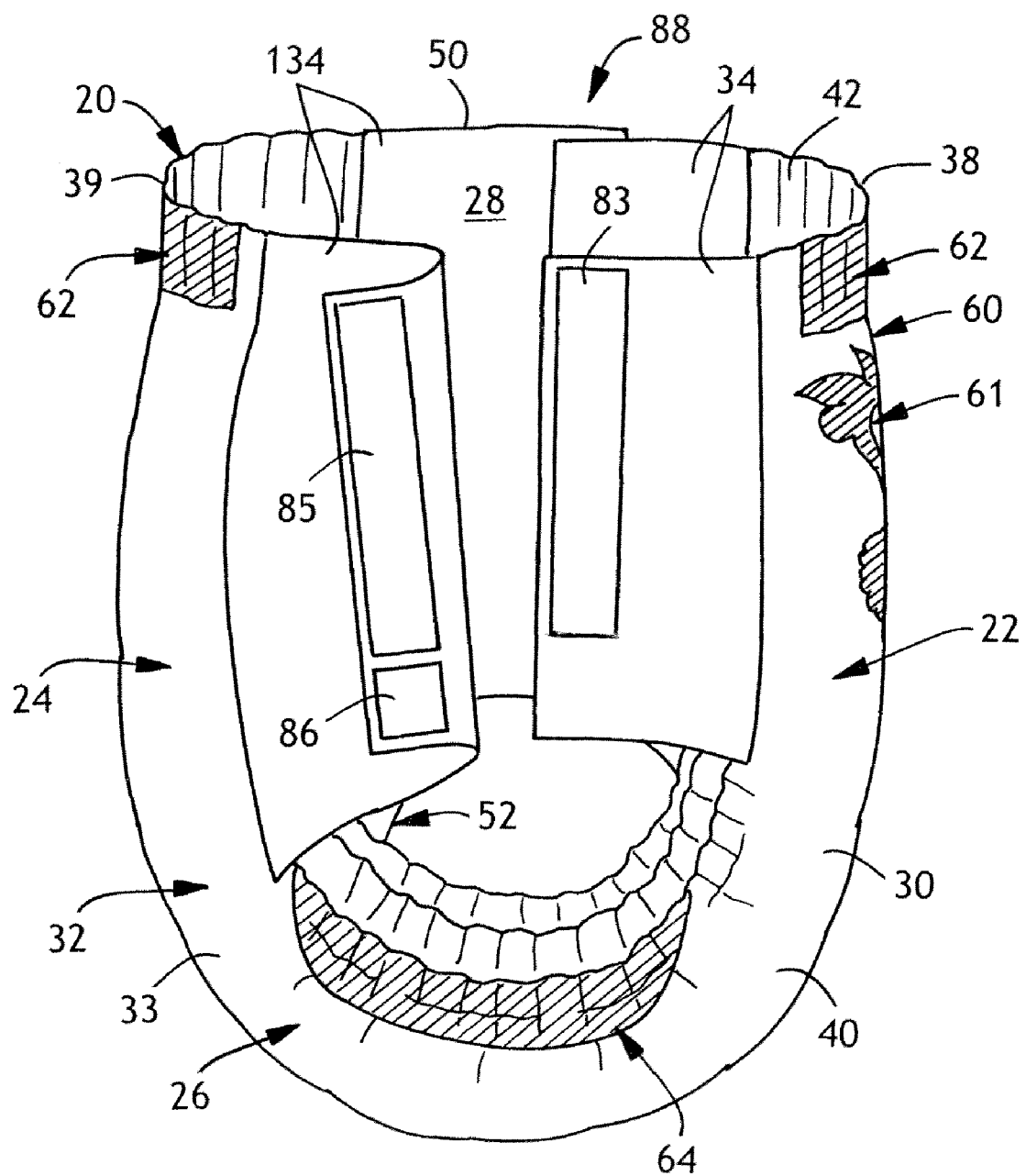
FIG. 1D illustrates a side view of an alternative disposable absorbent article incorporating the principles of the present invention, where the fastening system is shown engaged on one side of the absorbent article and disengaged on the other side of the absorbent article.
Figure 1E:
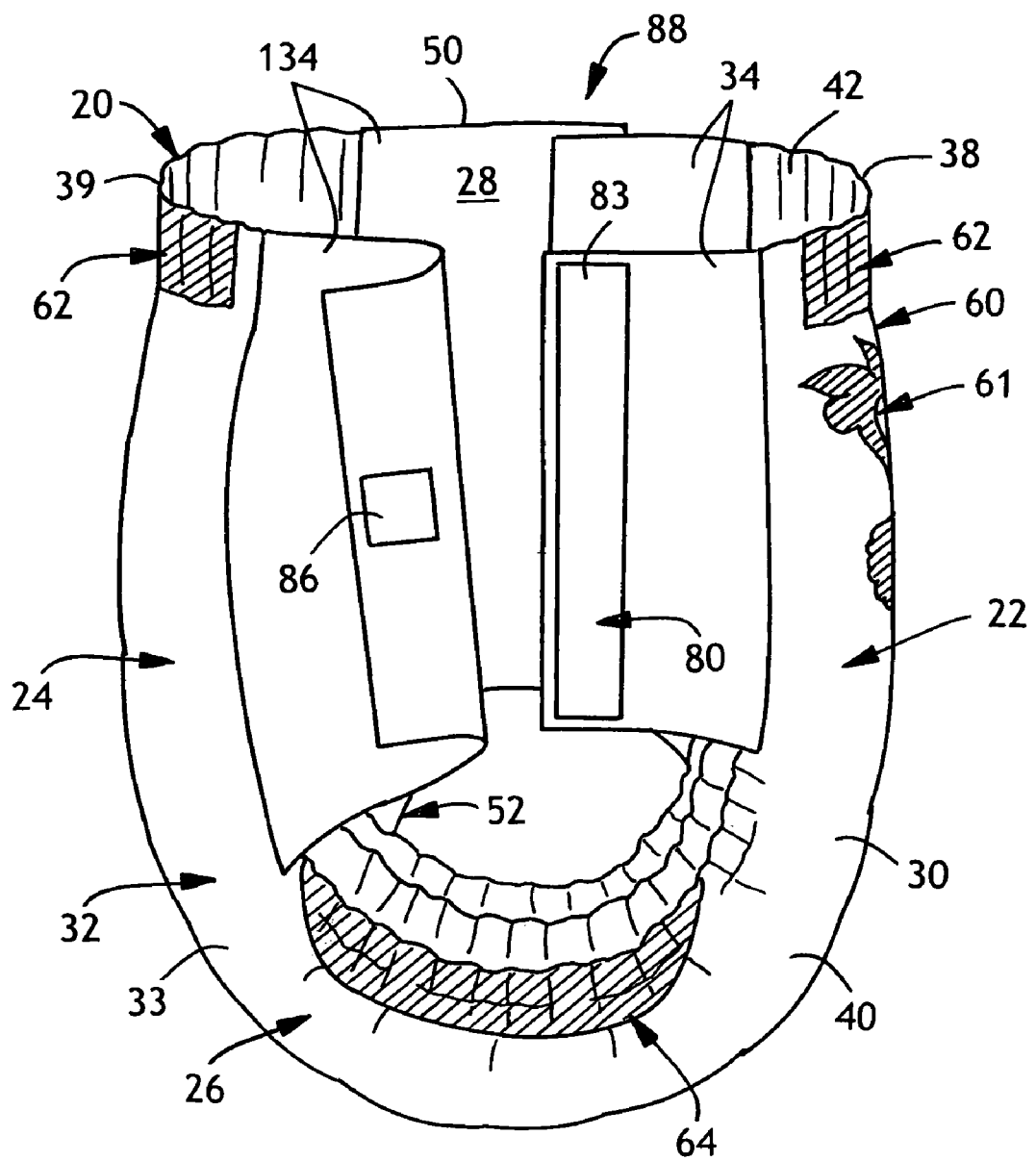
FIG. 1E illustrates a side view of an alternative disposable absorbent article incorporating the principles of the present invention, where the fastening system is shown engaged on one side of the absorbent article and disengaged on the other side of the absorbent article.
Figure 2:
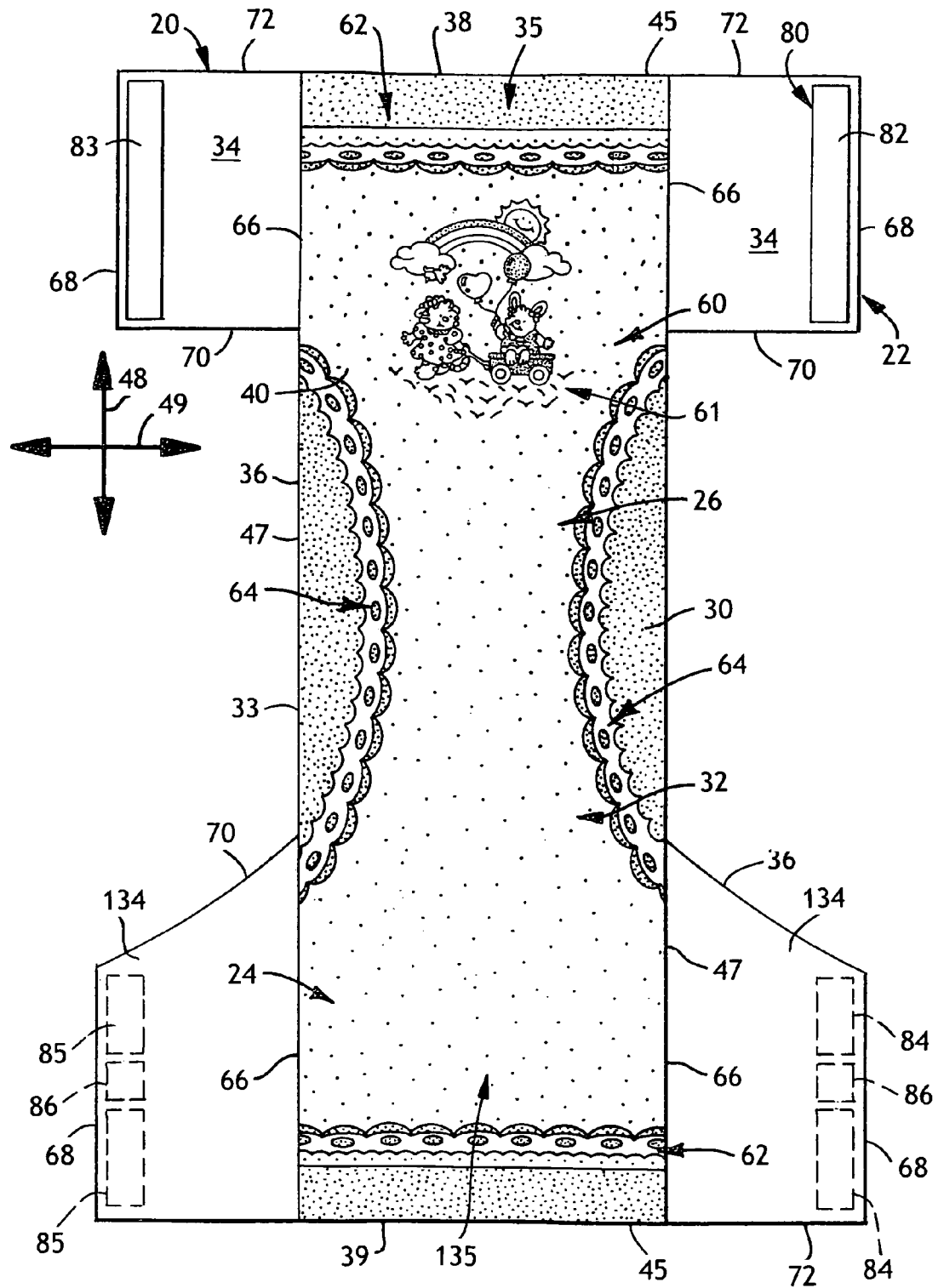
FIG. 2 illustrates a plan view of the disposable absorbent article shown in FIG. 1A in an unfastened, stretched and laid flat condition, and showing the surface of the article that faces away from the wearer.
Figure 3:
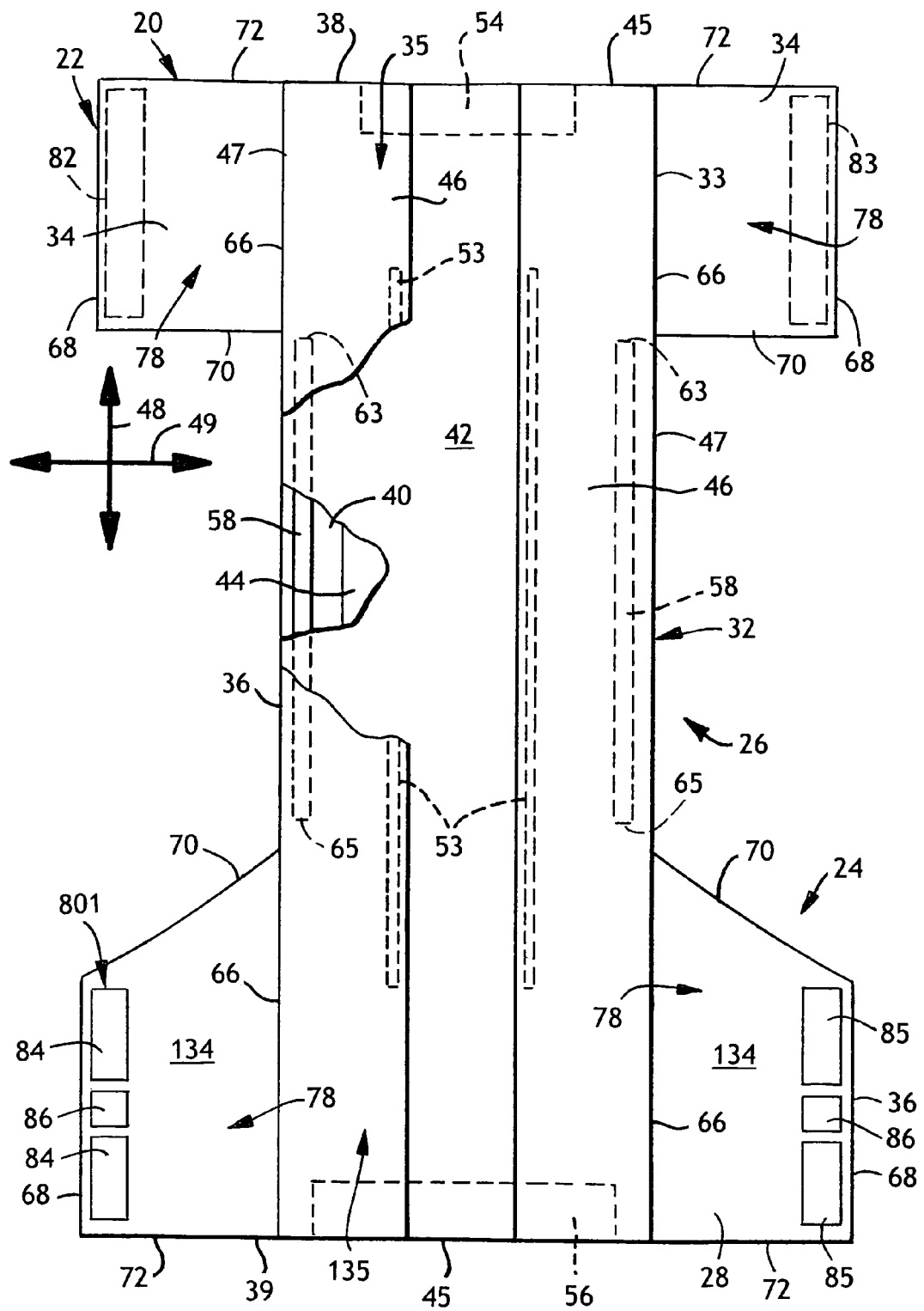
FIG. 3 illustrates a plan view similar to FIG. 2, but showing the surface of the article that faces the wearer when the article is worn, and with portions cut away to show the underlying features.

In the embodiments illustrated in FIGS. 1A, 1C, 2, 3, 4 and 6, the disposal fastener 86 contacts at least a portion of one of the first fasteners 82, 83 when the training pant 20 is prefastened. This configuration may provide two benefits. First, when the disposal fastener 86 and the first fasteners 82, 83 comprise resilient material and the absorbent article comprises stretchable material, the fastener 82, 83, 86 may restrict, or tie up some of the stretchable material. In these situations, it may be advantageous to minimize the amount of stretchable material that is restricted. By overlapping the disposal fastener 86 and one of the first fasteners 82, 83, the effective amount of material which is restricted is minimized. Further, as illustrated in FIG. 1A, one of the first fasteners 83 may completely overlie the disposal fastener 86 when the training pant 20 is prefastened, this may minimize the amount of material that is restricted. Secondly, when the disposal fastener 86 and the first fasteners 82, 83 comprise resilient material and the absorbent article comprises flexible material, the fastener 82, 83, 86 may inhibit the flexibility and drapability of the article. Again, overlapping the disposal fastener 86 and one of the first fasteners 82, 83 may minimize the amount of the article with reduced flexibility.

In the embodiments illustrated in FIGS. 1B and 1E, the disposal fastener 86 and the fastening components 82, 83 may be arranged such that when the waist end edge 72 in the front waist region 22 and the waist end edge 72 in the back waist region 24 are aligned, the disposal fastener 86 and the fastening components 82, 83 do not longitudinally overlap. In this orientation, the disposal fastener 86 may function as a compliment to the fastening components 82, 83 for securing the article about the waist of the wearer. Further, the disposal fastener 86 and the mating fastening components 84, 85 may be longitudinally aligned as illustrated in FIG. 1B. This configuration provides the similar benefits as described above with respect to flexibility, and reduction in stretchability, in addition, this configuration may present advantages in material utilization.

The refastenable seams 88 desirably extend substantially the entire distance between the waist opening 50 and the leg openings 52 when the fastening components 82-85 are engaged. More specifically, the refastenable seams 88 can cover about 75 to 100 percent, and particularly about 90 to about 98 percent, of the distance between the waist opening 50 and each leg opening 52, which distance is measured parallel to the longitudinal axis 48. To construct the seams 88 to extend substantially the entire distance between the waist and leg openings 50 and 52, the fastening components 82-85 can be formed to cover about 80 to 100 percent, and more particularly about 90 to about 98 percent, of the distance between the waist end edge 70 and the leg end edge 72 of the side panels 34 and 134.

The absorbent chassis 32 and the fastening system 80 together define a refastenable pant having a waist opening 50 and a pair of leg openings 52. When the fastening system is engaged, it can be appreciated that the refastenable pant includes a pair of elastomeric front side panels 34 extending from the waist opening to each leg opening, a pair of elastomeric back side panels 134 extending from the waist opening to each leg opening, a pair of refastenable seams 88 extending from the waist opening to each leg opening and positioned between the elastomeric front and back side panels, an elastomeric front waistband 54 disposed in the front waist region and positioned between the pair of elastomeric front side panels, an elastomeric back waistband 56 disposed in the back waist region and positioned between the pair of elastomeric back side panels, and a pair of elastomeric leg members 58 which partially encircle each leg opening. Each elastomeric leg member 58 extends from adjacent an elastomeric front side panel 34 in the front waist region 22 to adjacent an elastomeric back side panel 134 in the back waist region 24.

Figure 4:
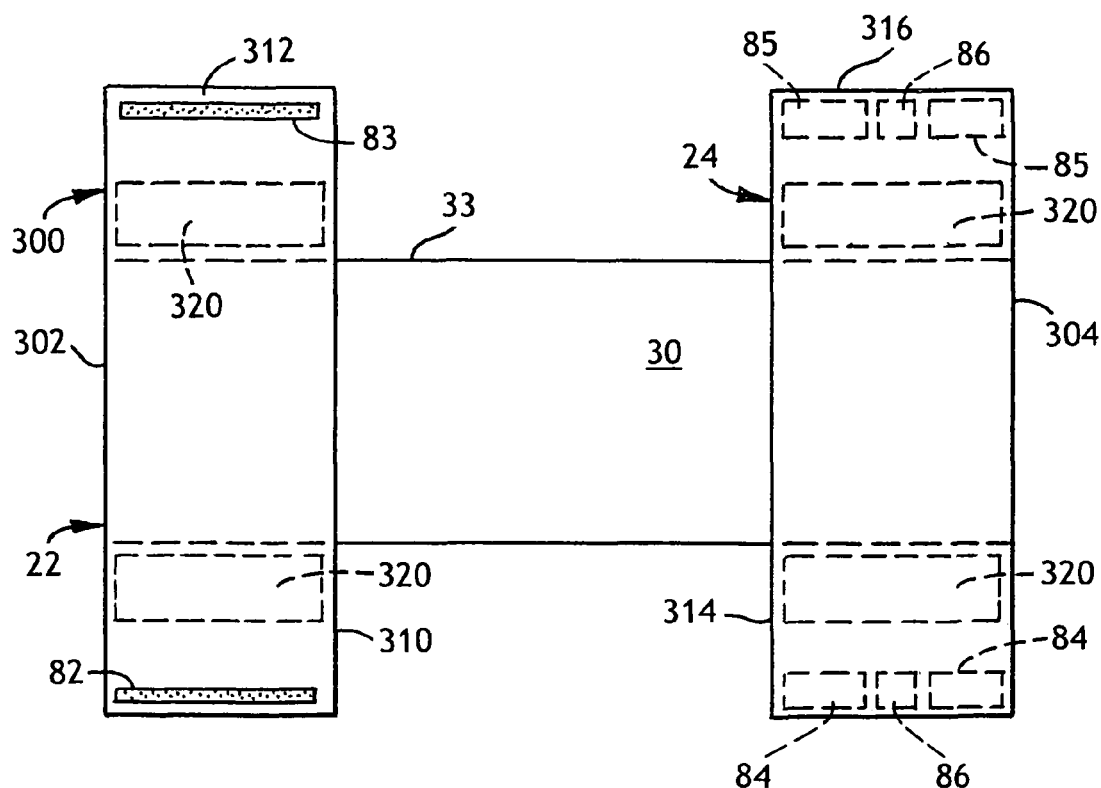
FIG. 4 illustrates a plan view of an alternative disposable absorbent article shown in an unfastened, stretched and laid flat condition, and showing the surface of the article that faces away from the wearer.

An alternative training pant 300 is illustrated in a stretched and laid flat condition in FIG. 4. The training pant 300 includes panel members 302 and 304 that are disposed respectively in the front and back waist regions 22 and 24. The panel member 302 in the front waist region 22 forms first and second side panels 310 and 312 that extend transversely outward from the composite structure 33 and the absorbent assembly 44 (FIG. 3). Similarly, the panel member 304 in the back waist region 24 forms first and second side panels 314 and 316 that extend transversely outward from the composite structure 33 and the absorbent assembly 44.

The training pant 300 also includes first and second fastening components 82 and 83 bonded to the inner surface 28 of the back attachment panels 314 and 316, and first and second mating fastening components 84 and 85 bonded to the outer surface 30 of the front attachment panels 310 and 312. In one particular embodiment, the fastening components 82 and 83 comprise loop type fasteners and the mating fastening components 84 and 85 comprise hook type fasteners that are directed outward, away from the body to minimize the chance of skin irritation. The training pant 300 may include any of the disposal fasteners 86 and 87 as described above with reference for FIGS. 1A-1E.

Figure 5:
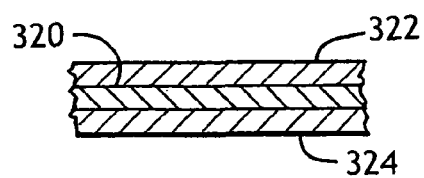
FIG. 5 illustrates an enlarged sectional view of a portion of a side panel of the absorbent article shown in FIG. 4.

The panel members 302 and 304 can each comprise an integral portion of a component of the composite structure 33, such as the bodyside liner 42 or a layer of the outer cover 40; or comprise a separate element bonded to the composite structure; or comprise a plurality of layers, whether integral portions, separate elements, or a combination thereof. Alternatively, the panel members 302 and 304 can represent portions of a single unitary member, such as a component of the composite structure 33, for example, an elastic or stretchable outer cover (not shown). The panel members 302 and 304 and thus the side panels 310, 312, 314 and 316 can comprise either elastic or inelastic materials. With additional reference to FIG. 5, the panel members 302 and 304 in the illustrated embodiment comprises a plurality of elastomeric segments 320 disposed between an outer facing layer 322 and an inner facing layer 324.

The elastomeric segments 320 can be positioned and arranged so that the side panels 310, 312, 314 and 316 have elastic properties in a direction generally parallel to the transverse axis 49 of the training pant 300. The elastomeric segments 320 can comprise elastomeric films, webs, strands, fibers or the like, and can comprise elastic materials similar to those described in relation to other elastic components of the training pants 20 and 300. The facing layers 322 and 324 can comprise materials of the type described in relation to the bodyside liner 42, the side panels 34, or the like.

Figure 6:
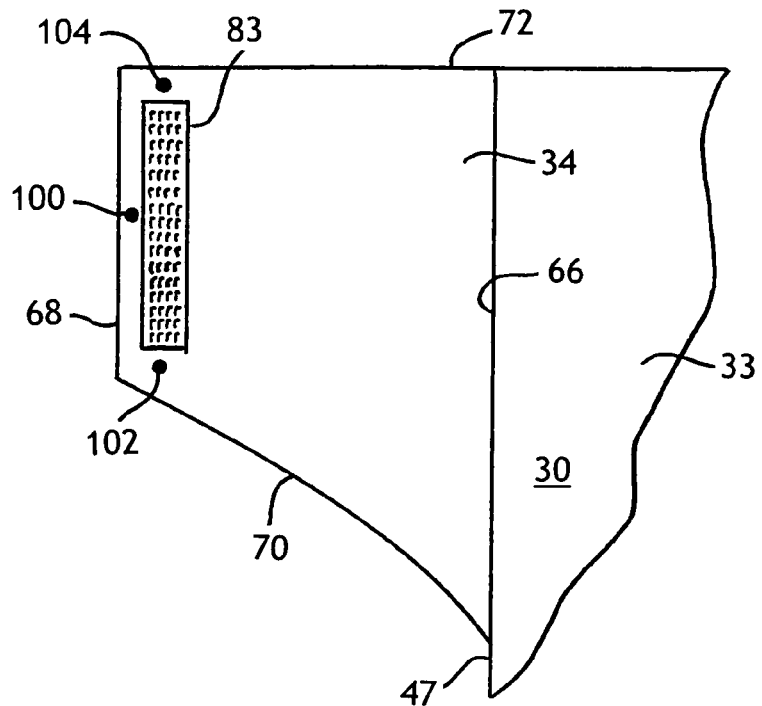
FIG. 6 illustrates an enlarged plan view of a side panel of the type shown in FIG. 1A.

An enlarged plan view of a side panel 34 of the type shown in FIG. 1 is illustrated in FIG. 6. Only one side panel 34 is shown in FIG. 6, although it should be understood that other side panels can employ a similar construction. The side panel 34 can be bonded to and extend transversely beyond the linear side edge 47 of the composite structure 33 along attachment line 66. The side panel 34 defines a distal edge 68 that is spaced from the attachment line 66, a leg end edge 70 disposed toward the longitudinal center of the training pant 20, and a waist end edge 72 disposed toward a longitudinal end of the training pant.

In particular embodiments, the fastening component 85 is spaced inward from the distal edge 68 and the end edges 70 and 72 in order to protect the wearer from irritation that might be caused by contact with the fastening component. Specifically, the fastening component 85 can be spaced transversely inward from the distal edge 68 in the region of reference numeral 100. Also, the fastening component 85 can be spaced longitudinally inward from the leg end edge 70 in the region of reference numeral 102, and spaced longitudinally inward from the waist end edge 72 in the region of reference numeral 104.

The degree of spacing balances the fact that a smaller distance is harder for children and parents to remove but provides a more garment-like appearance, while a larger distance is easier for children and parents to remove but provides a loose and floppy appearance that is not garment-like. Thus, the fastening component 85 is desirably spaced transversely inward from the distal edge 68 by about 1 to about 15 millimeters, particularly about 1 to about 5 millimeters, such as about 2 millimeters. The fastening component 85 is desirably spaced longitudinally inward from the leg end edge 70 and from the waist end edge 72 by about 2 millimeters or more, particularly about 5 millimeters or more, such as from about 5 to about 15 millimeters.

Figure 7:
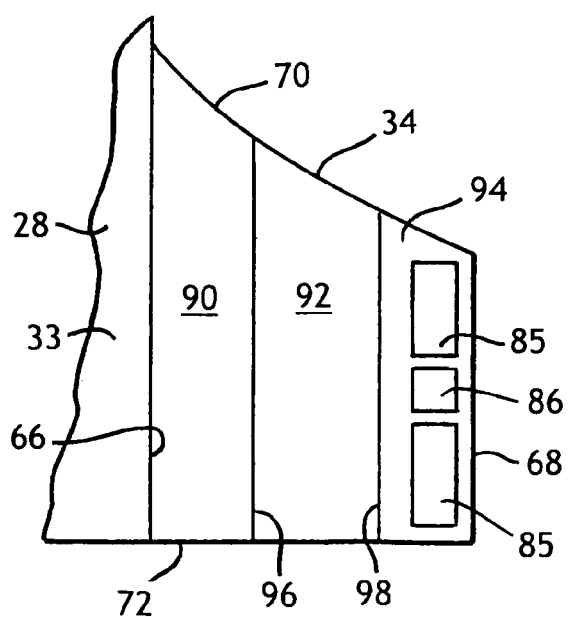
FIG. 7 illustrates an enlarged plan view of a portion of an alternative side panel.

A single side panel 34 of an alternative disposable absorbent article is shown in FIG. 7. The side panel 34 is bonded to a composite structure 33 at an attachment line 66. The side panel 34 includes a distal edge 68 transversely spaced from the attachment line 66 and a leg end edge 70 and a waist end edge 72 that extend from the composite structure to the distal edge. The side panel 34 illustrated in FIG. 7 includes a separate first member 90, second member 92, and third member 94 that are arranged in series from the attachment line 66 to the distal edge 68. The fastening component 83 is disposed on the third member 94 adjacent the distal edge 68.

The first member 90 is attached to the second member 92 at a seam 96, and the second member is attached to the third member 94 at a seam 98. The illustrated seams 96 and 98 extend from the leg end edge 70 to the waist end edge 72 of the side panel 34. The seams may be permanent seams or manually tearable seams. Suitable permanent seams can be formed by adhesives, sonic or thermal bonds, or some combination thereof, and are designed to resist tearing. Suitable manually tearable seams can be formed using means such as ultrasonic bonds to permit the side panel 34 to be torn easily at or along the seam by the caregiver. Such seams are suitably formed as lap seams or fin seams. In particular embodiments, the first and second members 90 and 92 comprise elastomeric materials and the third member 94 comprises a non-elastomeric material. Alternatively, the side panel may comprise two members, one or both of which may be elastomeric, that are bonded together at either a tearable seam or a permanent seam (not shown).

Figure 8:
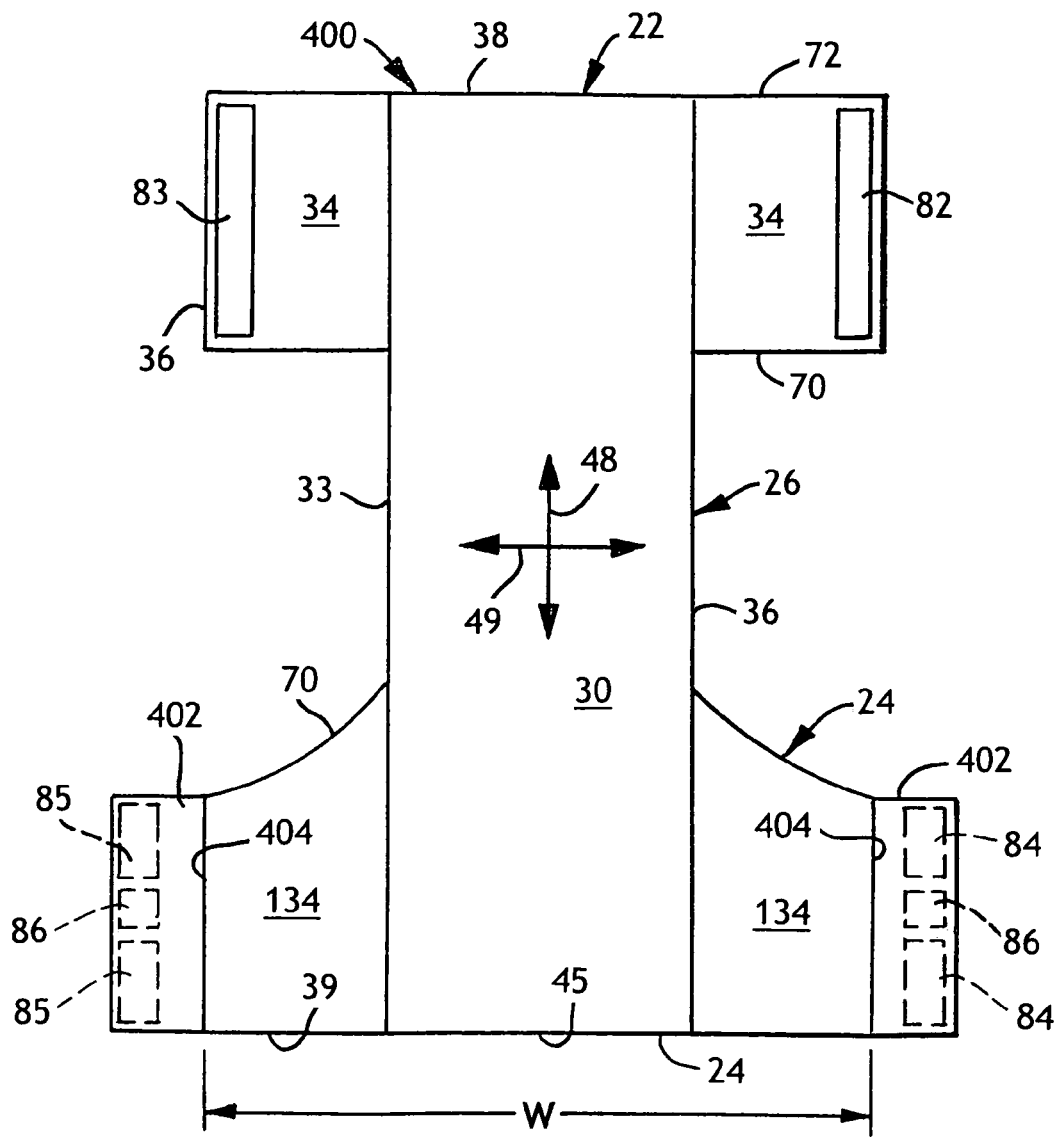
FIG. 8 illustrates a plan view of a further alternative disposable absorbent article shown in an unfastened, stretched and laid flat condition, and showing the surface of the article that faces away from the wearer.

A further alternative training pant 400 is illustrated in a stretched and laid flat condition in FIG. 8. The training pant 400 includes an absorbent chassis defining a longitudinal axis 48, a transverse axis 49, front and back waist edges 38 and 39 parallel to the transverse axis, and opposite side edges 36 extending between the front and back waist edges. The training pant 400 has a front waist region 22 contiguous with the front waist edge 38, a back waist region 24 contiguous with the back waist edge 39, and a crotch region 26 which extends between and interconnects the front and back waist regions. The illustrated absorbent chassis includes a rectangular composite structure 33, with a pair of elastomeric front side panels 34 bonded to the composite structure in the front waist region 22 and a pair of elastomeric back side panels 134 bonded to the composite structure in the back waist region 24. Desirably, the side panels 34 in the front waist region 22 are longitudinally spaced from the side panels 134 in the back waist region 24.

The illustrated training pant 400 also includes a pair of support members 402 that are bonded to and extend transversely outward from the back side panels 134. The support members 402 desirably although not necessarily comprise inelastic materials that are bonded to the side panels 134 at seams 404 using adhesives, sonic or thermal bonds, or the like. Alternatively, the training pant 400 can include support members 402 that are bonded to and extend transversely outward from both the front and back side panels 34 and 134, or from the front side panels alone (not shown).

The fastening system for the training pant 400 includes first and second fastening components 82 and 83 disposed on the support members 402. The fastening components 82 and 83 are adapted to releasably engage first and second mating fastening components 84 and 85 that are connected to the respective front side panels 34. The fastening components 82 and 83 can comprise separate structures bonded to the support members 402 or comprise integral portions, surfaces or regions of the support members. For instance, the support members 402 can comprise loop materials that function as the fastening components 82 and 83. For improved manufacturing performance, the width of the elastomeric side panels 34 in the front waist region 22 is equal to the width of the elastomeric side panels 134 in the back waist region 24. The width of the side panels 34 and 134 is represented in FIG. 8 by arrow W and excludes the width of the support members 402. The training pant 400 may include any of the disposal fasteners 86 and 87 as described above with reference for FIGS. 1A-1E.

The training pants 20, 300 and 400 can further include releasable side bonds (not shown) for improved reliability of maintaining the pant in a prefastened condition particularly when it is being pulled on or off over the hips of the wearer. Such releasable side bonds are desirably configured to be readily broken such that the caregiver can easily remove the training pant 20 after it has been soiled. The releasable side bonds desirably comprise ultrasonic point bonds. Absorbent articles including such releasable side bonds are further described in U.S. Pat. No. 6,287,287" issued Sep. 11, 2001 to Elsberg, which is incorporated herein by reference.

As described herein, the various components of the training pants 20, 300 and 400 can be integrally assembled together employing various types of suitable attachment means, such as adhesive, sonic and thermal bonds or combinations thereof.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed:

1. An absorbent article, comprising:

an absorbent chassis defining a longitudinal axis, a transverse axis, front and back waist edges parallel to the transverse axis, opposite side edges extending between the front and back waist edges, a front waist region contiguous with the front waist edge, a back waist region contiguous with the back waist edge, a crotch region which extends between and interconnects the front and back waist regions, an inner surface and an outer surface, the absorbent chassis comprising:

a rectangular composite structure having opposite linear side edges parallel to the longitudinal axis and opposite linear end edges parallel to the transverse axis, the composite structure comprising a bodyside liner, an outer cover bonded to the bodyside liner, and an absorbent assembly disposed between the bodyside liner and the outer cover;

first and second front side panels bonded to the composite structure in the front waist region, each front side panel having a distal edge, an interior portion between the distal edge and the composite structure, a waist end edge parallel to the transverse axis and forming part of the front waist edge, and a leg end edge forming part of the side edge, the front side panels having an average length dimension that is about 20 percent or greater of the overall length dimension of the absorbent article;

first and second back side panels bonded to the composite structure in the back waist region and longitudinally spaced from the first and second front side panels, each back side panel having a distal edge, an interior portion between the distal edge and the composite structure, a waist end edge parallel to the transverse axis and forming part of the back waist edge, and a leg end edge forming part of the side edge, the back side panels having an average length dimension that is about 20 percent or greater of the overall length dimension of the absorbent article;

a pair of first fasteners disposed on the first and second front side panels, each first fastener being adapted to engage at least a portion of the inner surface of the back waist region, each first fastener comprising a resilient material, the first fasteners having a length in the longitudinal direction that is greater than about 50% of the length dimension of the distal edge of the front side panels; and a pair of disposal fasteners disposed on the first and second back side panels, each disposal fastener adapted to engage at least a portion of the outer surface, each disposal fastener comprising a resilient material, the disposal fasteners having a length in the longitudinal direction that is less than about 25% of the length dimension of the distal edge of the back side panels, wherein the transverse distance between the pair of first fasteners is substantially equal to the transverse distance between the pair of disposal fasteners.

2. The absorbent article of claim 1 wherein each disposal fastener is configured to contact at least a portion of one of the first fasteners when the absorbent article is prefastened.

3. The absorbent article of claim 1 wherein each of the first fasteners completely overlies a disposal fastener when the absorbent article is prefastened.

4. The absorbent article of claim 1 wherein the pair of first fasteners and the pair of disposal fasteners are comprised of a similar material.

5. The absorbent article of claim 1 wherein the pair of first fasteners comprise a hook material and the pair of disposal fasteners comprise a hook material.

6. The absorbent article of claim 1 wherein each disposal fastener has a length-to-width ratio of about 2 or less and each first fastener has a length-to-width ratio of about 5 or greater.

7. The absorbent article of claim 1 wherein a ratio of the first fasteners area to the disposal fasteners area is greater than about 5:1.

8. An absorbent article, comprising:
an absorbent chassis defining a longitudinal axis, a transverse axis, front and back waist edges parallel to the transverse axis, opposite side edges extending between the front and back waist edges, a front waist region contiguous with the front waist edge, a back waist region contiguous with the back waist edge, a crotch region which extends between and interconnects the front and back waist regions, an inner surface and an outer surface, the absorbent chassis comprising:
a rectangular composite structure having opposite linear side edges parallel to the longitudinal axis and opposite linear end edges parallel to the transverse axis, the composite structure comprising a bodyside liner, an outer cover bonded to the bodyside liner, and an absorbent assembly disposed between the bodyside liner and the outer cover;
first and second front side panels bonded to the composite structure in the front waist region, each front side panel having a distal edge, an interior portion between the distal edge and the composite structure, a waist end edge parallel to the transverse axis and forming part of the front waist edge, and a leg end edge forming part of the side edge, the front side panels having an average length dimension that is about 20 percent or greater of the overall length dimension of the absorbent article;
first and second back side panels bonded to the composite structure in the back waist region and longitudinally spaced from the first and second front side panels, each back side panel having a distal edge, an interior portion between the distal edge and the composite structure, a waist end edge parallel to the transverse axis and forming part of the back waist edge, and a leg end edge forming part of the side edge, the back side panels having an average length dimension that is about 20 percent or greater of the overall length dimension of the absorbent article;

a pair of first fasteners disposed on the first and second front side panels, each first fastener being adapted to engage at least a portion of the inner surface of the back waist region, each first fastener comprising a resilient material, the first fasteners having a length in the longitudinal direction that is greater than about 50% of the length dimension of the distal edge of the front side panels; and a pair of disposal fasteners disposed on the first and second back side panels, each disposal fastener adapted to engage at least a portion of the outer surface, each disposal fastener comprising a resilient material, the disposal fasteners having a length in the longitudinal direction that is less than about 25% of the length dimension of the distal edge of the back side panels.

9. The absorbent article of claim 8 wherein each disposal fastener is configured to contact at least a portion of one of the first fasteners when the absorbent article is prefastened.

10. The absorbent article of claim 8 wherein each of the first fasteners completely overlies a disposal fastener when the absorbent article is prefastened.

11. The absorbent article of claim 8 wherein the first fasteners comprise a hook material and the disposal fasteners comprise a hook material.

12. The absorbent article of claim 8 wherein the first fasteners are disposed on the outer surface of the first and second front side panels, and the disposal fasteners are disposed on the inner surface of the back side panels.

13. The absorbent article of claim 8 wherein each disposal fastener is positioned equidistant between the waist end edge and the leg end edge along the distal edge of each back side panel.

14. An absorbent article, comprising:
an absorbent chassis defining a longitudinal axis, a transverse axis, first and second waist edges parallel to the transverse axis, opposite side edges extending between the first and second waist edges, a first waist region contiguous with the first waist edge, a second waist region contiguous with the second waist edge, a crotch region which extends between and interconnects the first and second waist regions, an inner surface and an outer surface, the absorbent chassis comprising:
a rectangular composite structure having opposite linear side edges parallel to the longitudinal axis and opposite linear end edges parallel to the transverse axis, the composite structure comprising a bodyside liner, an outer cover bonded to the bodyside liner, and an absorbent assembly disposed between the bodyside liner and the outer cover;
first and second first side panels bonded to the composite structure in the first waist region, each first side panel having a distal edge, an interior portion between the distal edge and the composite structure, a waist end edge parallel to the transverse axis and forming part of the first waist edge, and a leg end edge forming part of the side edge, the first side panels having an average length dimension that is about 20 percent or greater of the overall length dimension of the absorbent article;
first and second side panels bonded to the composite structure in the second waist region and longitudinally spaced from the first and second first side panels, each second side panel having a distal edge, an interior portion between the distal edge and the composite structure, a waist end edge parallel to the transverse axis and forming part of the second waist edge, and a leg end edge forming part of the side edge, the second side panels having an average length dimension that is about 20 percent or greater of the overall length dimension of the absorbent article;

a pair of first fasteners disposed on the first and second first side panels, each first fastener being adapted to engage at least a portion of the inner surface of the second waist region, each first fastener comprising a resilient material, the first fasteners having a length in the longitudinal direction that is greater than about 50% of the length dimension of the distal edge of the first side panels; and a pair of disposal fasteners disposed on the first and second side panels, each disposal fastener adapted to engage at least a portion of the outer surface, each disposal fastener comprising a resilient material, the disposal fasteners having a length in the longitudinal direction that is less than about 25% of the length dimension of the distal edge of the second side panels.

15. The absorbent article of claim 14 wherein each disposal fastener is configured to contact at least a portion of one of the first fasteners when the absorbent article is prefastened.

16. The absorbent article of claim 14 wherein each of the first fasteners completely overlies a disposal fastener when the absorbent article is prefastened.

17. The absorbent article of claim 14 wherein the first fasteners comprise a hook material and the disposal fasteners comprise a hook material.

18. The absorbent article of claim 14 wherein the first fasteners are disposed on the outer surface of the first and second first side panels, and the disposal fasteners are disposed on the inner surface of the second side panels.

19. The absorbent article of claim 14 wherein each disposal fastener is positioned equidistant between the waist end edge and the leg end edge along the distal edge of each second side panel.

20. An absorbent article, comprising:

an absorbent chassis defining a longitudinal axis, a transverse axis, front and back waist edges parallel to the transverse axis, opposite side edges extending between the front and back waist edges, a front waist region contiguous with the front waist edge, a back waist region contiguous with the back waist edge, a crotch region which extends between and interconnects the front and back waist regions, an inner surface and an outer surface, the absorbent chassis comprising:

a rectangular composite structure having opposite linear side edges parallel to the longitudinal axis and opposite linear end edges parallel to the transverse axis, the composite structure comprising a bodyside liner, an outer cover bonded to the bodyside liner, and an absorbent assembly disposed between the bodyside liner and the outer cover;

first and second front side panels bonded to the composite structure in the front waist region, each front side panel having a distal edge, an interior portion between the distal edge and the composite structure, a waist end edge parallel to the transverse axis and forming part of the front waist edge, and a leg end edge forming part of the side edge, the front side panels having an average length dimension that is about 20 percent or greater of the overall length dimension of the absorbent article;

first and second back side panels bonded to the composite structure in the back waist region and longitudinally spaced from the first and second front side panels, each back side panel having a distal edge, an interior portion between the distal edge and the composite structure, a waist end edge parallel to the transverse axis and forming part of the back waist edge, and a leg end edge forming part of the side edge, the back side panels having an average length dimension that is about 20 percent or greater of the overall length dimension of the absorbent article;

a pair of first fasteners disposed on the first and second front side panels, each first fastener being adapted to engage at least a portion of the outer surface of the back waist region, each first fastener comprising a resilient material, the first fasteners having a length in the longitudinal direction that is greater than about 50% of the length dimension of the distal edge of the front side panels; and a pair of disposal fasteners disposed on the first and second back side panels, each disposal fastener adapted to engage at least a portion of the outer surface, each disposal fastener comprising a resilient material, the disposal fasteners having a length in the longitudinal direction that is less than about 25% of the length dimension of the distal edge of the back side panels.

21. The absorbent article of claim 20 wherein the first fasteners comprise a hook material and the disposal fasteners comprise a hook material.

22. The absorbent article of claim 20 wherein the first fasteners are disposed on the inner surface of the first and second front side panels, and the disposal fasteners are disposed on the inner surface of the first and second back side panels.

23. The absorbent article of claim 20 wherein each disposal fastener is positioned equidistant between the waist end edge and the leg end edge along the distal edge of each back side panel.

* * * * *